US009895128B2

(12) United States Patent
Takahashi et al.

(10) Patent No.: US 9,895,128 B2
(45) Date of Patent: Feb. 20, 2018

(54) X-RAY CT APPARATUS AND CORRECTION PROCESSING DEVICE

(71) Applicant: HITACHI, LTD., Tokyo (JP)

(72) Inventors: Hisashi Takahashi, Tokyo (JP); Taiga Goto, Tokyo (JP); Koichi Hirokawa, Tokyo (JP)

(73) Assignee: HITACHI, LTD., Tokyo (JP)

(*) Notice: Subject to any disclaimer, the term of this patent is extended or adjusted under 35 U.S.C. 154(b) by 241 days.

(21) Appl. No.: 14/905,887

(22) PCT Filed: Aug. 6, 2014

(86) PCT No.: PCT/JP2014/070675
§ 371 (c)(1),
(2) Date: Jan. 18, 2016

(87) PCT Pub. No.: WO2015/020072
PCT Pub. Date: Feb. 12, 2015

(65) Prior Publication Data
US 2016/0157809 A1    Jun. 9, 2016

(30) Foreign Application Priority Data

Aug. 8, 2013   (JP) .................................. 2013-165190

(51) Int. Cl.
*A61B 6/00*       (2006.01)
*A61B 6/03*       (2006.01)

(52) U.S. Cl.
CPC ............ *A61B 6/5258* (2013.01); *A61B 6/032* (2013.01); *A61B 6/542* (2013.01); *A61B 6/5205* (2013.01); *A61B 6/544* (2013.01)

(58) Field of Classification Search
CPC ....... A61B 6/032; A61B 6/5258; A61B 6/542; A61B 6/03; A61B 6/5205; A61B 6/544; G06T 11/005
See application file for complete search history.

(56) References Cited

U.S. PATENT DOCUMENTS 4,761,819 A * 8/1988 Denison ................... G06K 9/40
                                                        382/128
6,529,575 B1   3/2003 Hsieh
(Continued)

FOREIGN PATENT DOCUMENTS

JP   H11-66311      3/1999
JP   2001-175863    6/2001
(Continued)

OTHER PUBLICATIONS

International Search Report in PCT/JP2014/070675, dated Nov. 11, 2014.

*Primary Examiner* — Glen Kao
(74) *Attorney, Agent, or Firm* — Cooper & Dunham LLP

(57) ABSTRACT

In order to provide a technique for reducing system noise from an output signal value (measurement data), an X-ray CT apparatus includes an X-ray generation unit that irradiates X-rays to an object, an X-ray detector that detects the X-rays transmitted through the object, a correction processing unit that corrects an output signal from the X-ray detector, and a reconstruction calculating unit that reconstructs an image on the basis of an output from the correction processing unit, in which the X-ray detector includes arranged detection elements, and in which the correction processing unit maintains an average value of output signal values of a plurality of predetermined detection elements centering on a focused detection element among the detection elements, and also reduces a variance of the output signal values of the plurality of predetermined detection elements centering on the focused detection element.

16 Claims, 9 Drawing Sheets

(56) References Cited

U.S. PATENT DOCUMENTS

| | | | |
|---|---|---|---|
| 2009/0168951 A1 | 7/2009 | Yan | |
| 2010/0098310 A1* | 4/2010 | Toth | A61B 5/411 |
| | | | 382/131 |
| 2010/0208113 A1* | 8/2010 | Kyushima | G06T 1/0007 |
| | | | 348/302 |
| 2014/0301625 A1* | 10/2014 | Takahashi | A61B 6/5258 |
| | | | 382/132 |
| 2016/0192896 A1* | 7/2016 | Perkins | G01T 1/2985 |
| | | | 250/252.1 |

FOREIGN PATENT DOCUMENTS

| | | |
|---|---|---|
| JP | 2004-585 | 1/2004 |
| JP | 2009-160394 | 7/2009 |
| JP | 2013-119021 | 6/2013 |

\* cited by examiner

X-RAY CT APPARATUS AND CORRECTION PROCESSING DEVICE

TECHNICAL FIELD

The present invention relates to an X-ray CT apparatus, and particularly to a noise reduction technique which is suitable for an apparatus having an automatic exposure control function of adjusting an X-ray irradiation dose during scanning.

BACKGROUND ART

An X-ray CT apparatus irradiates X-rays from the vicinity of an object, and generates a distribution of an X-ray absorption coefficient of the object as an image on the basis of projection data acquired at a plurality of projection angles. As an X-ray irradiation dose becomes larger, an image with less noise can be acquired, and thus image quality is improved. On the other hand, in recent years, an influence of exposure to X-rays on the human body has become problematic, and thus techniques have been actively examined in which image quality for a doctor to perform diagnosis is obtained even in a case where an X-ray irradiation dose is minimized. As one of the techniques, an automatic exposure control (AEC) technique of adjusting an X-ray irradiation dose during scanning according to information such as a size of an object or a scanning part, and image quality desired by an operator is widely known (PTL 1). As an index of the X-ray irradiation dose which is controlled in the AEC technique, a tube current-time product which is a product of a current (hereinafter, referred to as a tube current) applied to an X-ray tube and time (hereinafter, referred to as scan time) for a scanner to rotate one time is generally used.

CITATION LIST

Patent Literature

[PTL 1] Japanese Patent No. 4920256

SUMMARY OF INVENTION

Technical Problem

Noise (measurement noise) of measurement data obtained by the X-ray CT apparatus is roughly classified into photon noise which is statistical fluctuation of X-ray photons and system noise which is incorporated into a data acquisition system. The former increases in proportion to the tube current, but the latter is an amount of noise specific to the data acquisition system without depending on the tube current. In other words, a contribution of the system noise and the photon noise to the measurement noise differs depending on the magnitude (that is, the magnitude of an irradiation dose) of the tube current, and further a contribution thereof to image noise differs.

As an example, in scanning under a condition 1 of a tube current $mA_1$ and a scan time $t_1$, and a condition 2 of a tube current $mA_2$ and a scan time $t_2$, a case is assumed in which tube current-time products in both of the conditions are the same as each other ($mA_1 \times t_1 = mA_2 \times t_2$), and $mA_1 > mA_2$. In this case, focusing on photon noise, total amounts of irradiated X-ray photons are the same as each other in both of the conditions, and thus image noises are equivalent to each other. In other words, whereas, in the former, a lot of X-ray photons are irradiated for a short period of time, in the latter, a small amount of photons are irradiated for a long period of time, and thus irradiation amounts during scanning are equivalent to each other.

Since a ratio of the system noise to the photon noise is higher in the condition 2 than in the condition 1, a level of the entire noise of image data increases in the condition 2 even if the photon noises are equivalent to each other. In other words, in the former, a small amount of data having a great signal value is acquired, but, in the latter, a large amount of data having a small signal value is acquired. Therefore, an image created by using the latter data in which the system noise is mixed with individual data item by a predetermined amount is influenced by the system noise more than an image created by using the former data, regardless of the magnitude of the signal value.

As a result, even if the tube current-time products are the same as each other, a noise amount of image data and further quality of an obtained image differ. In the AEC technique of the prior art, only the photon noise is taken into consideration as a factor of image noise, and an irradiation dose is controlled by using a tube current-time product as an index. Therefore, even in a case where tube current-time products are the same as each other, actually obtained image quality may be greatly different from desired image quality in a scanning condition in which an influence of the system noise with respect to the photon noise cannot be disregarded.

An object of the present invention is to provide a technique of reducing system noise from an output signal value (measurement data).

Solution to Problem

In order to achieve the above-described object, according to the present invention, there is provided an X-ray CT apparatus including an X-ray generation unit that irradiates X-rays to an object; an X-ray detector that detects the X-rays transmitted through the object; a correction processing unit that corrects an output signal value from the X-ray detector; and a reconstruction calculating unit that reconstructs an image on the basis of an output from the correction processing unit. The correction processing unit maintains an average value of output signal values of a plurality of predetermined detection elements centering on a focused detection element, and also reduces a variance of the output signal values of the plurality of predetermined detection elements centering on the focused detection element.

Advantageous Effects of Invention

According to the present invention, it is possible to reduce system noise from an output signal value (measurement data).

DESCRIPTION OF EMBODIMENTS

Hereinafter, embodiments of the present invention will be described in detail with reference to the accompanying drawings.

Figure 1:
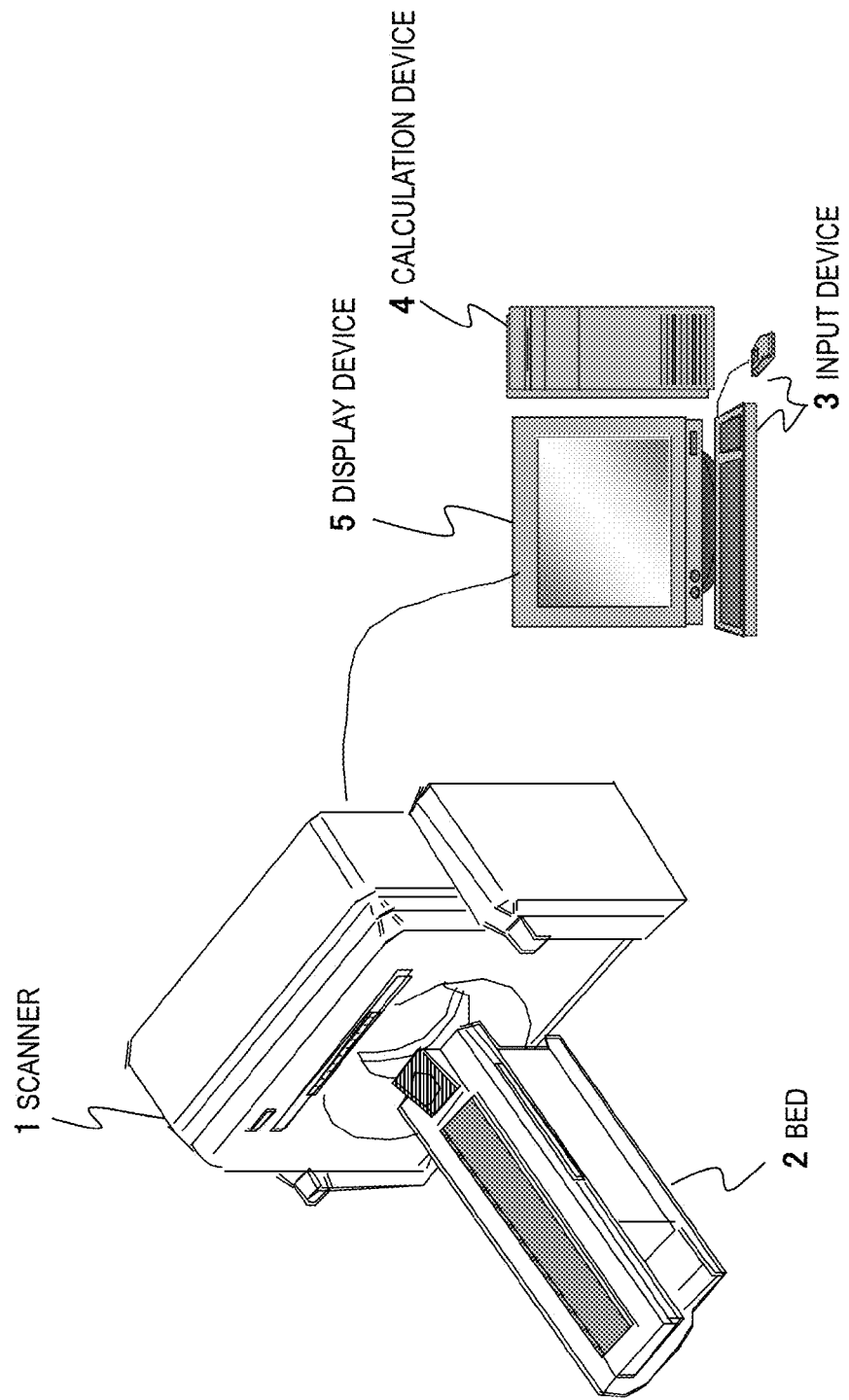
FIG. 1 is a perspective view illustrating an overview of the entire X-ray CT apparatus of an embodiment.
Figure 2:
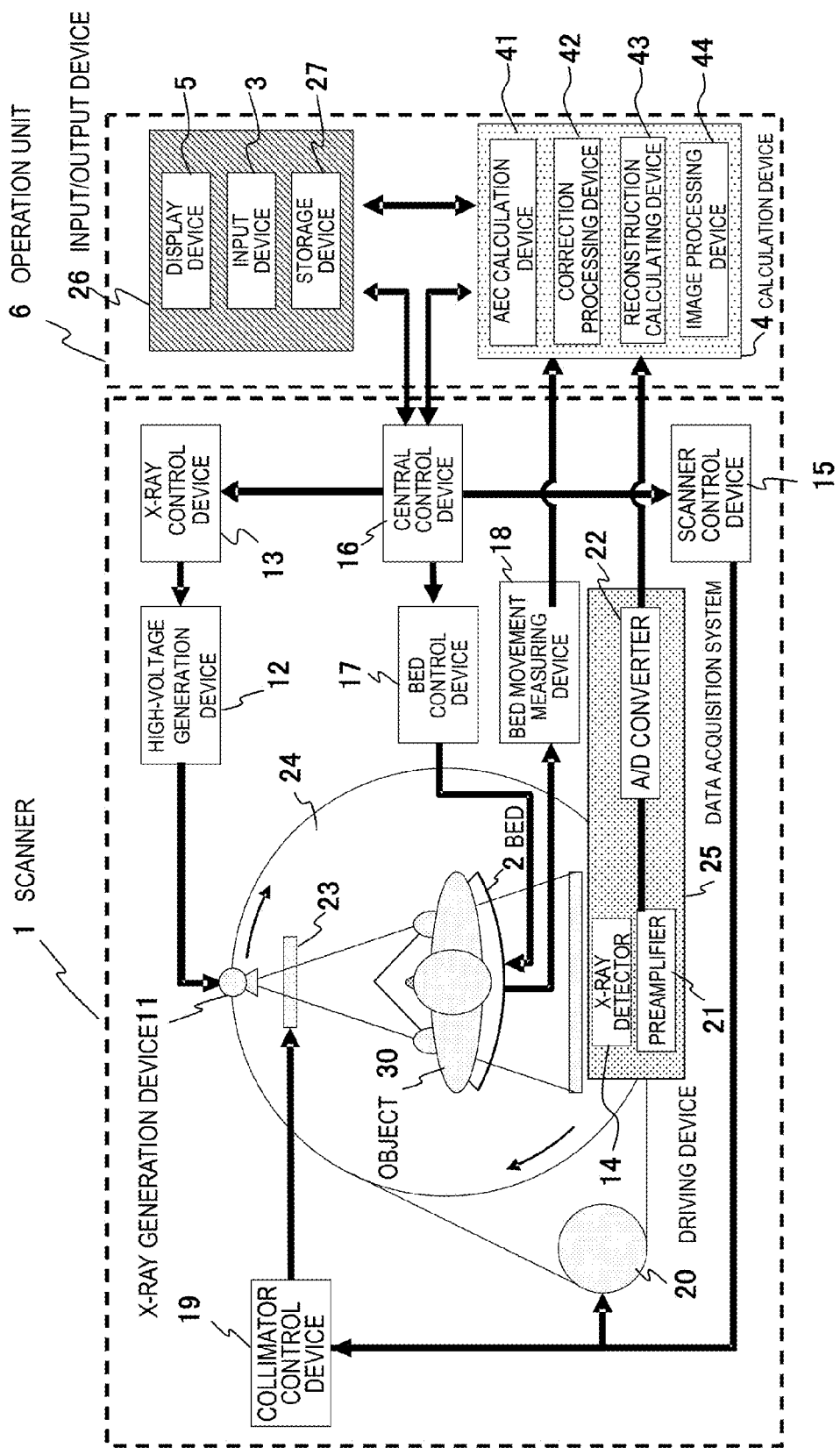
FIG. 2 is a block diagram illustrating the X-ray CT apparatus of the embodiment.

The present invention is configured to include, as illustrated in FIGS. 1 and 2, an X-ray generation unit (X-ray generation device 11) which irradiates X-rays to an object; an X-ray detector 14 which detects X-rays transmitted through an object 30; a correction processing unit (correction processing device 42) which corrects an output signal from the X-ray detector; and a reconstruction calculating unit (reconstruction calculating device 43) which reconstructs an image on the basis of an output from the correction processing unit (42). The X-ray detector 14 includes detection elements which are arranged in two-dimensional directions. The correction processing unit (42) maintains an average value of output signal values of a plurality of predetermined detection elements centering on a focused detection element and also reduces a variance of the output signal values of the plurality of predetermined detection elements centering on the focused detection element. Consequently, it is possible to reduce system noise from measurement data.

Specifically, the correction processing unit (42) obtains a value of each of a first evaluation function and a second evaluation function which have a corrected output signal value of the focused detection element as a variable, and obtains the corrected output signal value which causes a sum of the values to be the minimum through successive processes while changing the corrected output signal value. Here, as the first evaluation function, there is the use of a function in which a value of the first evaluation function becomes smaller as a difference between an uncorrected output signal value and a corrected output signal value of the focused detection element becomes smaller. As the second evaluation function, there is the use of a function in which a value of the second evaluation function becomes smaller as a difference between corrected output signal values of the focused detection element and a detection element adjacent thereto becomes smaller.

As the first evaluation function, there is the use of a function obtained by multiplying the square of the difference between the uncorrected output signal value and the corrected output signal value of the focused detection element by a predetermined coefficient T. The coefficient T may be determined on the basis of a value obtained by weighted-adding output signal values of a set of a focused detection element i and one or more detection elements j centering on the focused detection element. Specifically, for example, as the coefficient T, there may be the use of an average value of output signal values of the set of the focused detection element i and the one or more detection elements j centering on the focused detection element. As another example, as the coefficient T, there may the use of a value obtained by weighted-adding an output signal value of each of the one or more detection elements j according to a spatial distance between the detection element i and the detection element j.

As still another example, as the coefficient T, there may be the use of a value obtained by weighted-adding an output signal value of each of the one or more detection elements j on the basis of a correlation between an output signal value of the detection element i and an output signal value of the detection element j. In addition, as the coefficient T, there may be the use of a value obtained by assigning the value obtained through weighted-adding to a predetermined polynomial.

In addition, at least one of one or more predetermined detection elements j is adjacent to the focused detection element i in any one of channel, row, and view directions.

When obtaining the sum of the values of the first evaluation function and the second evaluation function, the correction processing unit (42) preferably performs weighted-adding by using a weighting factor β.

In addition, as the weighting factor β, a value is preferably used in which a variance of the corrected output signals obtained by the correction processing unit (42) is equal to or less than a predefined value with respect to a plurality of output signals of the detection elements obtained in a state in which X-rays irradiated to the object by the X-ray generation unit are shielded.

Further, when obtaining the sum of the values of the first evaluation function and the second evaluation function, the correction processing unit (42) performs weighted-adding by using a weighting factor α which is defined for each of the detection elements. As the weighting factor α, a value is preferably used which is becomes greater as an output signal value of the detection element is a non-positive number and an absolute value thereof becomes greater.

The correction processing unit (42) preferably performs correction of output signal values by sequentially shifting a focused detection element relative to a plurality of detection elements included in the X-ray detector 14.

The correction processing unit (42) of the present invention is suitable for being applied to an X-ray CT apparatus including an automatic exposure control calculation device that modulates a tube current for the X-ray generation unit during scanning according to information regarding an object.

Hereinafter, the X-ray CT apparatus according to an embodiment of the present invention will be described in more detail.

FIG. 1 is an exterior view of the X-ray CT apparatus of the embodiment, and FIG. 2 is a block diagram illustrating an internal configuration of the X-ray CT apparatus. The X-ray CT apparatus includes a scanner 1 used for scanning, a bed 2 on which an object is placed and which moves the object, an input device 3, a calculation device 4, and a display device 5. The input device 3 is constituted of a mouse or a keyboard, and receives inputting of measurement and reconstruction parameters such as bed movement speed information or a reconstruction position. The calculation device 4 processes data obtained from an X-ray detector 14 in the scanner 1. The display device 5 displays a reconstructed image. The input device 3 and the display device 5 constitute an input/output device 26 along with a storage device 27. The input/output device 26 and the calculation device 4 constitute an operation unit 6.

The scanner 1 includes an X-ray generation device 11, a data acquisition system 25, a collimator 23, and a rotary body 24 mounted with and rotates the above-described elements around the object 30. The data acquisition system 25 includes the X-ray detector 14, a preamplifier 21, and an A/D converter 22. In addition, the scanner 1 is configured to include a driving device 20 which rotatably drives the rotary body 24, a high-voltage generation device 12, an X-ray control device 13, a scanner control device 15, a central control device 16, a bed control device 17, a bed movement measuring device 18, a collimator control device 19, and the like.

The input device 3 of the operation unit 6 receives inputting of scanning conditions (a bed movement speed, a tube current, a tube voltage, a slice position, and the like) or reconstruction parameters (a region of interest, a reconstructed image size, a reverse projection phase width, a reconstruction filter function, and the like). On the basis of the received scanning conditions, control signals required for scanning are sent from the central control device 16 to the X-ray control device 13, the bed control device 17, and the scanner control device 15, and an operation for scanning is started by receiving a scanning start signal.

Specifically, a control signal is sent from the X-ray control device 13 to the high-voltage generation device 12, and the high-voltage generation device 12 applies a high voltage to the X-ray generation device 11. Consequently, the X-ray generation device 11 irradiates the object 30 with X-rays. Simultaneously, a control signal is sent from the scanner control device 15 to the driving device 20 so that the rotary body 24 mounted with the X-ray generation device 11, the X-ray detector 14, the preamplifier 21, and the like is rotated around the object 30. On the other hand, the bed control device 17 stops the bed 2 on which the object is placed, or moves the bed in a body axis direction.

An irradiation region of the X-rays emitted from the X-ray generation device 11 is restricted by the collimator 23, and thus the X-rays are irradiated to the object 30. The X-rays are absorbed (attenuated) by each tissue of the object 30, passes through the object 30, and are then detected by the X-ray detector 14. In addition, the X-ray detector 14 includes a plurality of detection elements which are arranged in two-dimensional directions (a channel direction and a row direction perpendicular thereto). Detection of a signal in the X-ray detector 14 is performed at discrete positions (view) in the rotation direction of the rotary body 24.

A detection signal of the X-ray detector 14 is converted into a current so as to be amplified by the preamplifier 21, and the current is converted into a digital signal by the A/D converter 22 so as to be output to the calculation device 4.

The calculation device 4 includes an AEC calculation device 41, a correction processing device 42, a reconstruction calculating device 43, and an image processing device 44. An output signal from the data acquisition system 25 undergoes logarithmic transform and various corrections in the correction processing device 42 of the calculation device 4, and is preserved in the storage device 27 of the input/output device 26 as projection data. The reconstruction calculating device 43 of the calculation device 4 performs an image reconstruction process by using the preserved projection data so as to generate a reconstructed image. The reconstructed image is preserved in the storage device 27 of the input/output device 26 and is also displayed as a CT image on the display device 5.

A brief description will be made of an operation in which the AEC calculation device 41 performs automatic exposure control. When setting scanning conditions, if an operator inputs an instruction for execution of AEC and an image quality index via the input device 3, the AEC calculation device 41 performs an operation for the automatic exposure control. As the image quality index, any one of all well-known indexes represented by image noise may be used. The AEC calculation device 41 calculates control information regarding a tube current in scanning by appropriately using the image quality index, a perspective image of the object at any scanning angle, acquired in advance, and the scanning conditions. The control information is sent to the X-ray control device 13 via the central control device 16, and irradiation with X-rays is performed on the basis of the control information. Consequently, an X-ray irradiation dose is adjusted (automatic exposure control) according to information such as a size of the object or a scanning part, and image quality desired by the operator, and scanning is performed.

A description will be made of a process of reducing system noise in the correction processing device 42.

Embodiment 1

The correction processing device 42 performs, on an output signal from the data acquisition system 25, a process of maintaining a local mean value of output signals of a plurality of predetermined detection elements centering on a focused detection element and of reducing a variance corresponding to a system noise amount included in the output signals of the plurality of predetermined detection elements.

Figure 3:
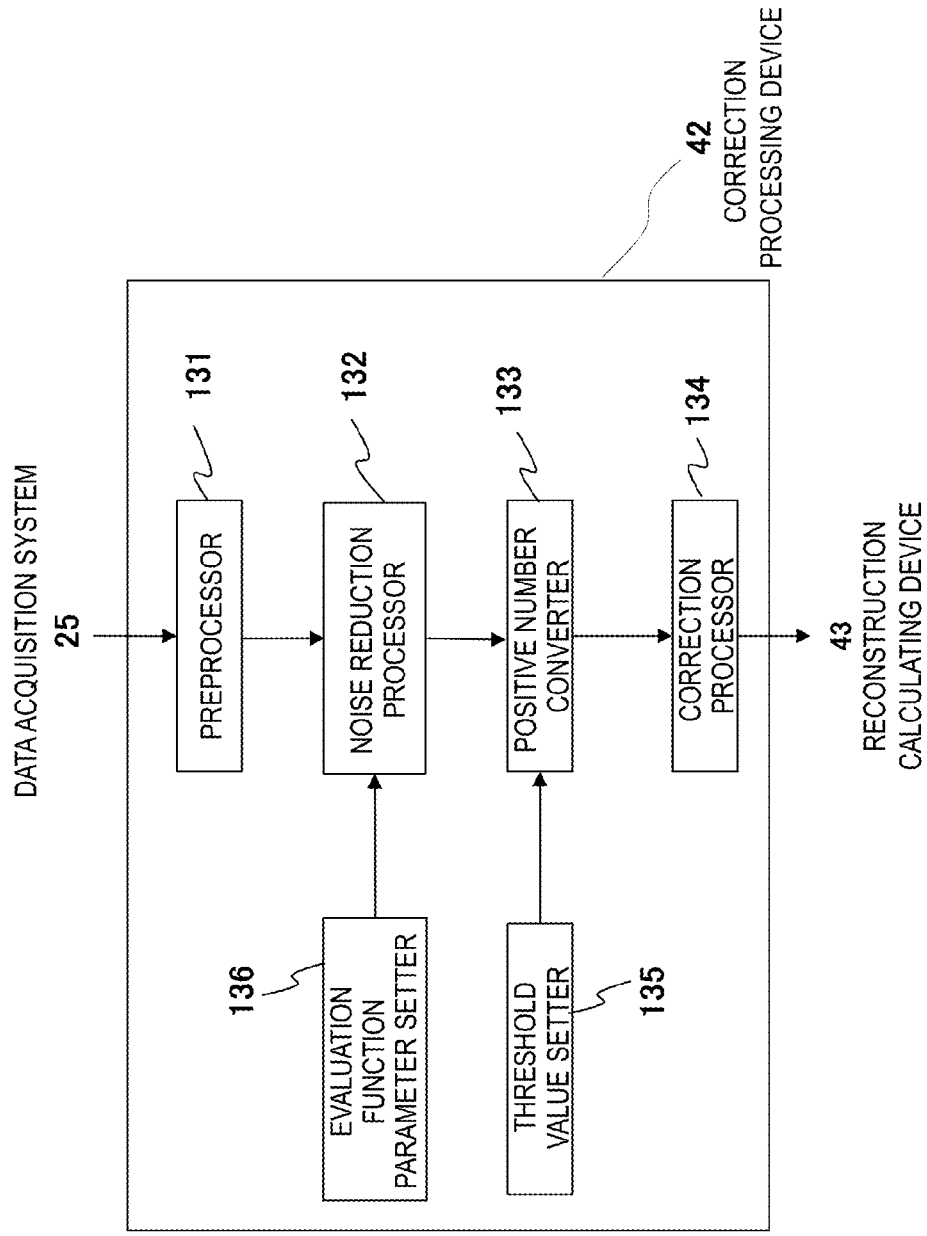
FIG. 3 is a block diagram illustrating a correction processing device 42 of Embodiment 1.
Figure 4:
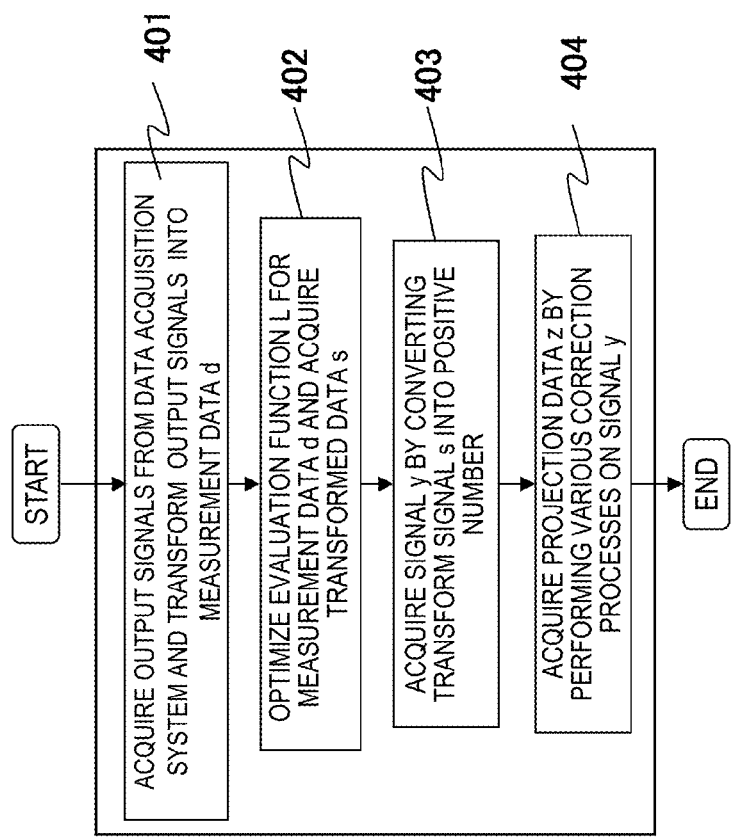
FIG. 4 is a flowchart illustrating an operation of the correction processing device of Embodiment 1.

FIG. 3 is a block diagram illustrating a specific configuration of the correction processing device 42, and FIG. 4 is a flowchart illustrating an operation of the correction processing device 42. As illustrated in FIG. 3, the correction processing device 42 is configured to include a preprocessor 131, a noise reduction processor 132, a positive number converter 133, a correction processor 134, an evaluation function parameter setter 136, and a threshold value setter 135. The above-described constituent elements may be constituted of hardware obtained through combination of circuit elements, and may be constituted of a CPU and a memory and may be operated by the CPU reading and executing a program in the memory.

In addition, in the following description, in order to differentiate output signals of a plurality of detection elements of the X-ray detector 14 from each other, numbers $(1, \ldots, i, \ldots, I)$ are given to output signals acquired in one scanning in three directions including the above-described channel, row, and view directions.

First, the preprocessor 131 receives output signals from the data acquisition system 25 and performs preprocessing thereon (a first step 401 in FIG. 4). Specifically, in a case where the signals are compressed when being transmitted from the data acquisition system 25, the output signals are restored to an original number of bits. In addition, offset correction is performed by respectively subtracting output signals (offset) acquired in a state in which exposure to X-rays is not performed, from the output signals. A signal value of an i-th output signal obtained as a result thereof is referred to as a measurement data $d_i$. Further, a set of measurement data acquired for all channel, row, and view directions through one scanning is indicated by $d = \{d_i | i=1, \ldots, I\}$.

Next, the noise reduction processor 132 performs a successive approximation process on the measurement data $d = \{d_i | i=1, \ldots, I\}$ so as to perform a process of maintaining a local mean value of the output signals of a plurality of predetermined detection elements centering on a focused detection element and of reducing a variance corresponding to a system noise amount included in the output signals of the plurality of predetermined detection elements (a second step 402). A set of corrected data (hereinafter, referred to as transformed data) is indicated by $s = \{s_i | i=1, \ldots, I\}$.

In the present embodiment, the noise reduction processor 132 obtains transformed data s which causes an evaluation function L(s) to be the minimum by using a penalized weighted least square (PWLS) function L(s) expressed in Equation (1). Consequently, the local mean value of the output signals is maintained, and the variance corresponding to the system noise amount is reduced.

[Equation 1]

$$L(s) = \sum_{i=1}^{I} f(T_i)(d_i - s_i)^2 + \beta \sum_{i=1}^{I} \sum_{j \in N_i} w_{ij}(s_i - s_j)^2 \quad (1)$$

In Equation (1), the first term is an evaluation function which has the transformed data $s_i$ as a variable and indicates the strength of restriction based on the measurement data, and depends on a difference $(d_i - s_i)$ between the measurement data $d_i$ and the transformed data $s_i$. The first term is referred to as a data fidelity term. Focusing on only the data fidelity term, a value (evaluation value) of the function of the first term becomes smaller as a difference between the transformed data $s_i$ and the measurement data $d_i$ becomes smaller (as an extreme example, when the transformed data $s_i$ is the same as the measurement data $d_i$, a value of the data fidelity term becomes the minimum).

In addition, in the present embodiment, $f(T_i)$ which is multiplied by the square of the difference $(d_i - s_i)$ in the data fidelity term is expressed as in the following Equation (2).

[Equation 2]

$$f(T_i) = T_i \quad (2)$$

$T_i$ in the data fidelity term is determined by a value obtained by weighted-adding the measurement data $d_i$ of the focused detection element i and measurement data $d_j$ of one or more predetermined detection elements j located therearound with a weighting factor $v_{ij}$. For example, $T_i$ obtained by using the following Equation (3) is used.

[Equation 3]

$$T_i = \frac{1}{\sum_{j \in M_i} v_{ij}} \sum_{j \in M_i} v_{ij} d_j \quad (3)$$

Figure 5:
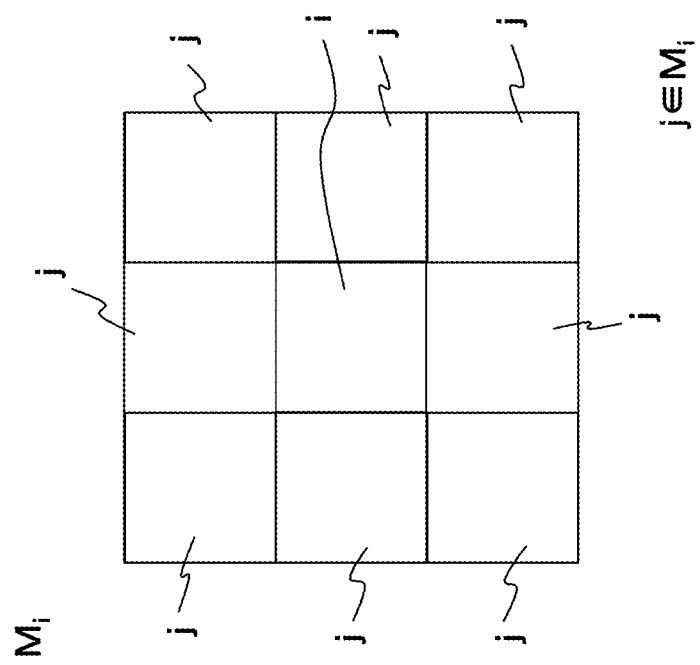
FIG. 5 is a diagram for explaining a positional relationship between detection elements of a set $M_t$ of Embodiment 1.

In Equation (3), a set $M_i$ is a set for defining the detection elements j whose measurement data $d_j$ is weight-summed, and, for example, is formed of the focused detection element i and one or more detection elements j located around the detection element i as illustrated in FIG. 5. In this case, at least one of the detection elements j is set to be adjacent to the focused element i in any one of the channel, row, and view directions. The set $M_i$ is defined in advance and is stored in the evaluation function parameter setter 136. The weighting factor $v_{ij}$ may be a constant, but a value defined by correlation between positions of the detection elements i and j may be used.

A method of defining a value of the weighting factor $v_{ij}$ will now be described by the following first to fourth examples. Any one of the first to fourth examples may be used in a predefined manner, and may be used by the noise reduction processor 132 receiving selection from a user via the input device 3.

The first example corresponds to a method of using a predefined constant as the weighting factor $v_{ij}$. For example, if $v_{ij}=1$, $T_i$ is an average value of the measurement data d of the focused detection element i and a detection element group (the detection element group included in the set $M_i$) located therearound. In a case of using a predefined constant as the weighting factor $v_{ij}$, a value of the weighting factor $v_{ij}$ is stored in the evaluation function parameter setter 136 in advance, and the noise reduction processor 132 reads and uses the value.

As the second to fourth examples, a description will be made of methods in which the noise reduction processor 132 obtains the weighting factor $v_{ij}$ through computation by using a correlation between positions of the detection elements i and j. In the second example, the weighting factor $v_{ij}$ is calculated on the basis of spatial distances between the detection element i and the detection elements j by using Equation (4). The weighting factor $v_{ij}$ defined by Equation (4) has a greater value by the detection element j closer to the focused detection element i.

[Equation 4]

$$v_{ij} = e^{-\frac{\|p_i - p_j\|^2}{2\gamma_d^2}} \quad (4)$$

In Equation (4), $p_i$ and $p_j$ are respectively coordinate vectors of the detection elements i and j, and are coordinate vectors having the same origin in the three-dimensional Euclid space. Therefore, $(p_i - p_j)$ indicates a spatial distance between the detection element i and the detection element j. $\gamma_d$ is an arbitrary parameter defining correlation of a spatial distance between the detection elements i and j, and is stored in the evaluation function parameter setter 136 as a constant in advance.

The third example corresponds to a method in which the weighting factor $v_{ij}$ is defined by using a correlation between the measurement data $d_i$ and $d_j$ according to Equation (5). The weighting factor $v_{ij}$ defined by Equation (5) has a greater value by the detection element j having the measurement data d closer to a value of the measurement data $d_i$ of the focused detection element i.

[Equation 5]

$$v_{ij} = e^{-\frac{\|d_i - d_j\|^2}{2\gamma_r^2}} \quad (5)$$

In Equation (5), $\gamma_r$ is an arbitrary parameter defining correlation between the measurement data $d_i$ and $d_j$ of the detection elements i and j, and is stored in the evaluation function parameter setter 136 as a constant in advance.

In the fourth example, the weighting factor $v_{ij}$ is defined on the basis of a positional correlation between the detection elements i and j and a correlation between the measurement data $d_i$ and $d_j$ according to Equation (6). Equation (6) indicates a bilateral filter, and the weighting factor $v_{ij}$ defined by Equation (6) has a greater value by the detection element j which is located nearer to the focused detection element i and has the measurement data $d_j$ closer to a value of the measurement data $d_i$ of the focused detection element i.

[Equation 6]

$$v_{ij} = e^{-\frac{\|p_i - p_j\|^2}{2\gamma_d^2}} e^{-\frac{\|d_i - d_j\|^2}{2\gamma_r^2}} \quad (6)$$

Next, the second term of Equation (1) will be described. The second term is an evaluation function which has the transformed data $s_i$ as a variable and indicates a correlation between transformed data $s_i$ and $s_j$ of the focused detection element i and the detection element j close thereto, and is referred to as a penalty term. The smaller value (evaluation value) of the penalty term indicates the higher correlation of signal values between the transformed data $s_i$ of the focused detection element i and the transformed data $s_j$ of the detection element j located therearound. In other words, in the second term, a value of the second term becomes smaller as a difference $(s_i-s_j)$ between values of the transformed data $s_i$ and the transformed data $s_j$ is reduced. Specifically, $(s_i-s_j)$ is weight-summed with a weighting factor $w_{ij}$, and is successively summed while changing a position of the focused detection element i. As an extreme example, when transformed data s of all detection elements has the same value, an evaluation value of the penalty term becomes the minimum.

In the second term of Equation (1), a set $N_i$ is a set for defining one or more detection elements j used for evaluation, and is formed of the focused detection element and one or more detection elements j located around the detection element i. In this case, at least one of the detection elements j is set to be adjacent to the detection element i in any one of the channel, row, and view directions. The set $N_i$ is defined in advance and is stored in the evaluation function parameter setter 136. The weighting factor $w_{ij}$ is a weighting factor with which the difference $(s_i-s_j)$ of the transformed data is weighted.

In the present embodiment, regarding the weighting factor $w_{ij}$, as shown in Equation (7), a value of each weighting factor $w_{ij}$ is defined in advance so that a sum of weighting factors $w_{ij}$ for each detection element j included in the set $N_i$ becomes 1. The value of $w_{ij}$ is stored in the evaluation function parameter setter 136 in advance.

[Equation 7]

$$\sum_{j \in N_i} w_{ij} = 1 \quad (7)$$

In addition, $\beta$ of Equation (1) is a parameter for determining balance between the data fidelity term of the first term and the penalty term of the second term, and is referred to as a penalty coefficient. Evaluation values of the data fidelity term and the penalty term are in a contrary relation, and thus whereas the data fidelity term becomes smaller as the transformed data $s_i$ has a value closer to the measurement data $d_i$, the penalty term becomes smaller as the difference $(s_i-s_j)$ of the transformed data $s_i$ and $s_j$ is reduced. For this reason, a relationship between both of the terms is adjusted by using the penalty coefficient $\beta$. As an extreme example, in a case where the penalty coefficient $\beta$ is 0, transformed data is determined by using only the data fidelity term, and in a case where the penalty coefficient $\beta$ is $\infty$, transformed data is determined by using only the penalty term.

The noise reduction processor 132 obtains an optimal penalty coefficient $\beta$ for each scanning condition in advance and stores the penalty coefficient in the evaluation function parameter setter 136. The noise reduction processor 132 reads the penalty coefficient $\beta$ corresponding to a scanning condition from the evaluation function parameter setter 136 and uses the penalty coefficient for calculation of the function L(s) of Equation (1).

Here, a description will be made of an operation in which the noise reduction processor 132 obtains the penalty coefficient $\beta$ along a flow illustrated in FIG. 6.

First, the noise reduction processor 132 instructs the central control device 16 to shield X-rays by completely closing an opening of the collimator 23 illustrated in FIG. 2 for each scanning condition and to perform predetermined scanning in this state. Output signals obtained by the data acquisition system 25 through the scanning include only system noise. Preprocessing (restoring of the number of bits, and offset correction) in the same manner as in the above-described step 401 is performed on the obtained output signals which are then transformed into measurement data (step 601). Herein, the obtained measurement data is referred to as noise measurement data.

Next, a value of the function L(s) of Equation (1) is calculated by using the noise measurement data obtained in step 601, the predefined provisional penalty coefficient $\beta$, and the above-described other parameters, and transformed data s={$s_i$|i=1, . . . , I} which causes the function L(s) to be the minimum is obtained through successive processes (step 602). In this case, the provisional penalty coefficient $\beta$ is set to a sufficiently small positive number.

As a method of obtaining the transformed data s through the successive processes in step 602, all well-known numerical value analysis methods may be employed, but, herein, as an example, the transformed data s is calculated by using a Gauss-Seidel method. Specifically, the transformed data s is calculated by using an update equation of Equation (8) derived by applying the Gauss-Seidel method to Equation (1).

[Equation 8]

$$s_i^{(p+1)} = \frac{T_i d_i + \beta \sum_{j \in N_i} w_{ij} s_j^{(p)}}{T_i + \beta \sum_{j \in N_i} w_{ij}} \quad (8)$$

In Equation (8), $s_i^{(p)}$ is transformed data $s_i$ obtained through a p-th successive process. In addition, the set $N_i$ is the same as the set $N_i$ defined in Equation (1). $T_i$ and $w_{ij}$ are defined according to the above Equations (3) and (7).

With reference to the flowchart illustrated in FIG. 7, a description will be made of a procedure of obtaining the transformed data $s_i$ through successive processes using Equation (8). First, in step 701, the noise measurement data $d_i$ of the detection element i, each parameter, and predefined initial data $s_i^{(0)}$ are assigned to Equation (8), and thus transformed data $s_i^{(1)}$ having undergone first update is calculated.

Next, in step 702, it is determined whether or not the transformed data $s_i^{(1)}$ having undergone the update satisfies a predefined convergence condition, and, if the data does not satisfy the convergence condition, the number of updates is updated to p+1 (=2) in step 704, the flow returns to step 701 in which $s_i^{(2)}$ is calculated through a second successive process. If the convergence condition is satisfied, the flow proceeds to step 703, and the transformed data $s_i^{(1)}$ is output as the transformed data $s_i$. This operation is repeatedly performed until the transformed data $s_i^{(p)}$ satisfying the convergence condition is obtained, and thus the transformed data $s_i$ can be obtained.

The determination of the convergence condition in step 702 is performed by determining whether or not a difference $(s_i^{(p)} - s_i^{(p-1)})$ of the transformed data between the updates is equal to or less than a preset threshold value. In a case where the difference $(s_i^{(p)} - s_i^{(p-1)})$ of the transformed data $s_i^{(p)}$ between the updates is equal to or less than a preset threshold value, it is determined that convergence has occurred.

This method is only an example, and other convergence conditions may be used. For example, a method is used in which the number of updates is counted in step 704, and an update is finished if the number of updates reaches a predefined number.

Figure 7:
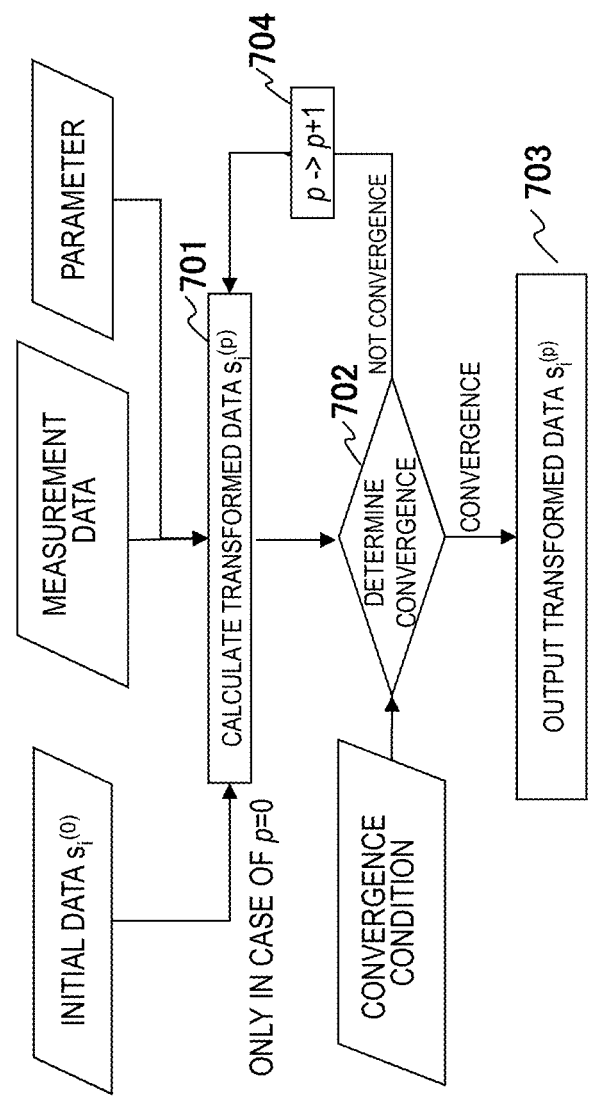
FIG. 7 is a flowchart illustrating an operation of obtaining transformed data of Embodiment 1.

The successive processes illustrated in FIG. 7 are performed for all detection elements, and thus the transformed data $s_i$ is obtained for each detection element. In addition, order of detection elements for obtaining transformed data may be arbitrary.

Through the above-described process, the transformed data $s = \{s_i | i=1, \ldots, I\}$ corresponding to the provisional penalty coefficient β is obtained. Next, the flow proceeds to step 603 of FIG. 6, and a variance of the transformed data $s = \{s_i | i=1, \ldots, I\}$ is obtained. The obtained variance is noise included in the transformed data of the noise measurement data. It is determined whether or not the obtained noise value is smaller than a predefined desired noise value (step S604). As the desired noise value, 0 or any positive value close to 0 is used.

In a case where the obtained noise value is smaller than the desired noise value, it is determined that the provisional penalty coefficient β is optimal β, and the process is finished (step 605).

On the other hand, in a case where the obtained noise value is greater than the desired noise value, any positive value is added to the provisional penalty coefficient β in order to correct β (step 606). Corrected β is used as the provisional penalty coefficient β, and the flow returns to step 602 so that the processes in steps 602 to 604 are repeatedly performed.

The above-described processes in steps 602 to 604 correspond to a method in which the penalty coefficient β is gradually increased from a positive number close to 0, and β obtained at the time when a noise value smaller than the desired noise value is obtained for the first time is determined as an optimal penalty coefficient β, but the present invention is not limited thereto, and a method may be used in which β is gradually decreased.

In addition, since the system noise changes depending on a rotation speed or a tube voltage, the noise reduction processor 132 obtains an optimal penalty coefficient β for each scanning condition in advance, and stores the optimal penalty coefficient in the evaluation function parameter setter 136.

If the noise reduction processor 132 receives the measurement data $d = \{d_i | i=1, \ldots, I\}$ from the preprocessor 131 in step 401 of FIG. 4, the noise reduction processor reads the adding factor $v_{ij}$, the set $M_i$, the coefficients $\gamma_d$ and $\gamma_r$, and the like, in a case of a constant, from the evaluation function parameter setter 136 as necessary, and obtains $T_i$ of Equation (3) through calculation. In addition, the obtained $T_i$, the penalty coefficient β, the adding factor $w_{ij}$, and the set $N_i$, which are read from the evaluation function parameter setter 136, and the measurement data d obtained in step 401, are assigned to Equation (1), so that the transformed data $s_i$ which causes the function L(s) of Equation (1) to become the minimum is obtained. A method of calculating the transformed data $s_i$ is the same as in the process described by using Equation (8) and FIG. 7, and the data is calculated through successive processes. Consequently, the transformed data $s_i$ is obtained for all detection elements i. The obtained transformed data $s = \{s_i | i=1, \ldots, I\}$ is data in which an average value of measurement data of the detection elements j within a predetermined range centering on the focused detection element i is maintained, and a value corresponding to a system noise amount is removed.

Next, the positive number converter 133 illustrated in FIG. 3 converts non-positive number transformed data $s_i$ into positive number data on the transformed data s calculated in the second step, so as to acquire positive number data $y = \{y_i | i=1, \ldots, I\}$ (the third step 403 in FIG. 4). This process enables the correction processor 134 to perform logarithmic transform in the next fourth step 404. For example, in a case where i-th transformed data $s_i$ has a non-positive number, the non-positive number transformed data $s_i$ is converted into positive number data by using a method of replacing the non-positive number with an average value of transformed data located therearound, or a method in which any preset threshold value is read from the threshold value setter 135, and if the transformed data $s_i$ is smaller than the threshold value, the transformed data $s_i$ is replaced with the threshold value.

Finally, the correction processor 134 illustrated in FIG. 3 performs, on the positive number data y converted by the positive number converter 133, a logarithmic transform process, reference correction using a value of a reference detector, air correction using data obtained through scanning when there is no object, phantom correction for minimizing an influence of a beam hardening effect, and the like, so as to obtain projection data $z = \{z_i | i=1, \ldots, I\}$ (fourth step 404). The projection data z is preserved in the storage device 27 of the input/output device.

The reconstruction calculating device 43 of the calculation device 4 performs an image reconstruction process by using the preserved projection data so as to generate a reconstructed image.

Figure 8:
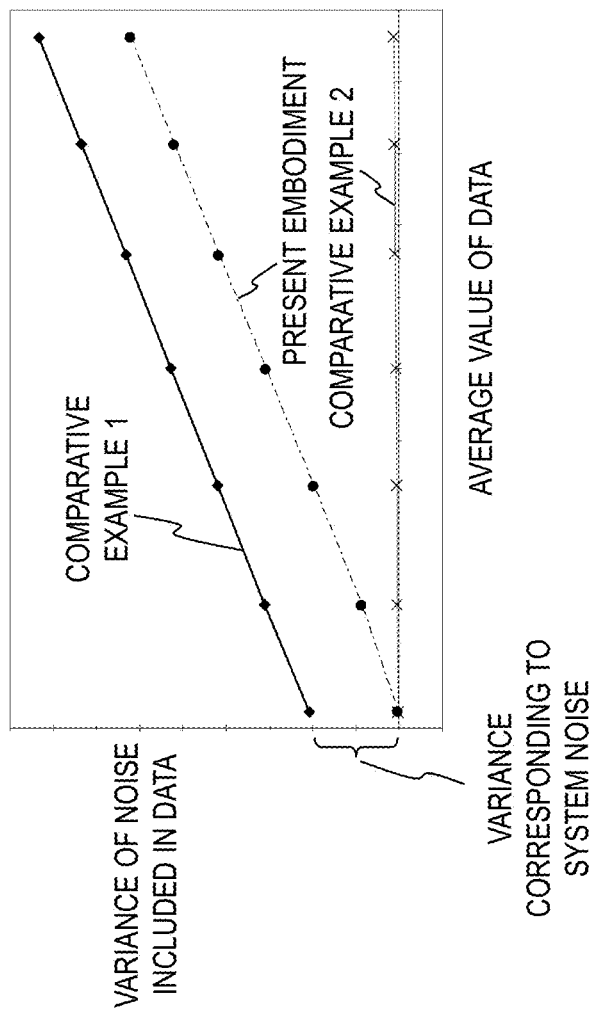
FIG. 8 is a graph illustrating an effect of the transformed data of Embodiment 1.

An effect of the present embodiment will be described with reference to a graph of FIG. 8. First, scanning for irradiating the same object with X-rays while changing tube currents was repeatedly performed multiple times (here, seven times), and output signals from the data acquisition system 25 were acquired. The processes in steps 401 to 403 of FIG. 4 were performed on each of the output signals obtained through the scanning performed for multiple times, and thus positive number data having undergone the noise reduction process of the present embodiment was obtained. An average value and a variance value of the obtained positive number data were calculated, and were plotted on the graph of FIG. 8 whenever the scanning is performed for seven times. In the graph of FIG. 8, a transverse axis expresses an average value of data, and a longitudinal axis expresses a variance value of noise.

In addition, as a comparative example 1, measurement data was obtained by performing only the process in step 401 on output signals from the data acquisition system 25. An average value and a variance value of the obtained data were calculated and were plotted on the graph of FIG. 8 whenever the scanning is performed for seven times.

Further, as a comparative example 2, a process using the penalized least square function, which is a general noise reduction process was performed on output signals from the data acquisition system 25 after step 401, and then the process in step 403 was performed thereon, so that positive number data was obtained. An average value and a variance value of the obtained positive number data were calculated and were plotted on the graph of FIG. 8 whenever the scanning is performed for seven times.

In the graph of FIG. 8, plotting at seven points for each of the present embodiment and the comparative examples 1 and 2 corresponds to scanning using seven types of tube currents.

It can be seen from the graph of FIG. 8 that the tube current and the mean value of the data have a substantially proportional relationship, and thus a magnitude relationship of the mean value of the data corresponds to a magnitude relationship of the tube current in all of the present embodiment, and the comparative examples 1 and 2.

When the graph of the comparative example 1 is compared with the graph of the present embodiment, it can be seen from the plotting obtained through the scanning using corresponding tube currents that the mean values of the data are substantially the same as each other, and thus the mean values are not changed through the process. Next, if a variance of noise of the comparative example 1 is focused, the variance has a certain degree of value even when the mean value of the data becomes to be almost 0, and this variance value is considered to contribute to only system noise. In a case where noise is reduced through the general noise reduction process of the comparative example 2, it can be seen that a variance is substantially 0 regardless of the mean value (that is, the tube current) of the data. This indicates that, in the noise reduction process of the comparative example 2, a variance of data which is equal to or more than a system noise value is reduced from the measurement data. In contrast, it can be seen from the graph of the present embodiment that the graph is obtained by moving the graph of the comparative example 1 substantially in parallel, and a variance corresponding to system noise is reduced regardless of the tube current.

As mentioned above, a variance corresponding to system noise can be removed from measurement data regardless of a tube current by performing the process in the noise reduction processor 132 of the present embodiment, and thus equivalent image quality can be realized if tube current-time products set by an operator are the same as each other. Therefore, in a case where the tube current-time products are the same as each other, even in a scanning condition in which an influence of system noise with respect to photon noise cannot be disregarded, obtained image quality does not greatly vary, and a reconstructed image with constant image quality can be provided. Therefore, the operator can easily expect image quality in advance. In addition, in a case where AEC is used, it is possible to achieve desired image quality with high accuracy according to the present invention even in a case where an influence of the system noise is unlikely to be escaped in the related art.

Embodiment 2

In Embodiment 2, the correction processing device 42 performs a process for achieving a desired noise reduction effect more accurately even in a case where an average of measurement data of detection elements j around a focused detection element i is considerably small.

A configuration of the correction processing device 42 of Embodiment 2 is the same as in FIG. 3 of Embodiment 1, and a flow of a process performed by the correction processing device 42 is the same as illustrated in FIG. 4. However, in Embodiment 2, Equation (9) is used instead of Equation (1) in step 402 of FIG. 4. Equation (9) relates to a PWLS function Q(s).

[Equation 9]

$$Q(s) = \sum_{i=1}^{I} f(T_i)(d_i - s_i)^2 + \sum_{i=1}^{I} \alpha_i \sum_{j \in N_i} w_{ij}(s_i - s_j)^2 \quad (9)$$

In Equation (9), symbols common to Equation (1) indicate the same parameters as in Embodiment 1. In Equation (9), $\alpha_i$, which is a penalty coefficient, is not equivalent for all data and is defined for each detection element i, and $\alpha_i$ is set to become greater as measurement data $d_i$ has a non-positive number and an absolute value thereof becomes greater. In the present embodiment, $\alpha_i$ is determined according to the measurement data $d_i$ for each detection element i by using the following Equation (10). In Equation (10), $\beta$ is the same parameter as $\beta$ in Embodiment 1.

[Equation 10]

$$\alpha_i = \begin{cases} \beta d_i^2 & (d_i < 0) \\ \beta & (d_i \geq 0) \end{cases} \quad (10)$$

As mentioned above, in Embodiment 2, the penalty coefficient $\alpha_i$ is set to become greater for each detection element i as the measurement data $d_i$ has a non-positive number and an absolute value thereof becomes greater, and thus the correction processing device 42 can reduce system noise more accurately even in a case where an average of measurement data of the detection elements j around the focused detection element i is considerably small.

Other configurations and processing operations are the same as in Embodiment 1, and thus description thereof will be omitted.

Embodiment 3

In a case where an X-ray absorption coefficient of an object does not depend on energy of X-rays, a relationship between an average value and a variance of data can be represented as a straight line as in the comparative example 1 in FIG. 8. In contrast, in a case where the X-ray absorption coefficient considerably depends on the energy, a relationship between both of the two is not represented as a straight line (called a beam hardening effect). Therefore, in Embodiment 3, the correction processing device 42 performs a process for realizing a desired noise reduction effect more accurately by taking into consideration an influence of the beam hardening effect of X-rays detected by the X-ray detector 14.

A configuration of the correction processing device 42 of Embodiment 3 is the same as in FIG. 3 of Embodiment 1, and a flow of a process performed by the correction processing device 42 is the same as illustrated in FIG. 4. However, in Embodiment 3, Equation (11) is used instead of Equation (1) in step 402 of FIG. 4. Equation (11) relates to a PWLS function R(s).

[Equation 11]

$$R(s) = \sum_{i=1}^{I} f(T_i)(d_i - s_i)^2 + \beta \sum_{i=1}^{I} \sum_{j \in N_i} w_{ij}(s_i - s_j)^2 \quad (11)$$

In Equation (11), symbols common to Equation (1) indicate the same parameters as in Embodiment 1. In Equation (11), f (T$_i$) which is multiplied by (d$_i$−s$_i$)$^2$ in the data fidelity term is a polynomial determined by taking into consideration the above-described beam hardening effect and is calculated as in the following Equation (12).

[Equation 12]

$$f(T_i) = -\theta_0 + \sum_{b=0}^{B} \theta_b T_i^b \qquad (12)$$

In Equation (12), B is an order of a polynomial, and θ$_b$ is a coefficient of a term with an order of b. Orders and coefficients of the polynomial of Equation (12) are determined on the basis of a relationship between an average value and a variance of data measured by using, for example, a plurality of water phantoms having different diameters.

First, the water phantoms having different diameters are irradiated with X-rays, and thus output signals from the data acquisition system 25 are acquired. The process in step 401 of FIG. 4 is performed on each of the obtained output signals, and thus measurement data is obtained. An average value and a variance of the obtained data are calculated.

A relationship between the calculated mean value and variance is plotted exactly in the same manner as in the comparative example 1 illustrated in FIG. 8. Therefore, orders and coefficients of the above-described polynomial are determined so that errors of the plotted graph and the polynomial are reduced by using, for example, a least square method. At this time, since an amount of calculation based on Equation (11) increases as an order becomes larger, the order is set to be equal to or smaller than 8. However, in a case where the above-described error is sufficiently small, as small an order as possible is selected.

Among the coefficients of the polynomial determined in the above-described way, θ$_0$ indicates a variance at T$_i$ of 0, that is, a variance corresponding to system noise. Since a desired process in step 402 of FIG. 4 is aimed at reducing a variance corresponding to system noise, a value obtained by subtracting θ$_0$ from the polynomial as in Equation (12) is used as f(T$_i$). In addition, coefficients and orders of the polynomial are stored in advance in the evaluation function parameter setter 136 illustrated in FIG. 3, and, for example, the noise reduction processor 132 reads and uses the coefficients and the orders of the polynomial in the same manner as parameters such as the penalty coefficient β. Further, as described above, system noise changes depending on a rotation speed or a tube voltage, and thus coefficients and orders of the polynomial are determined for each scanning condition, and are stored and used.

In the above-described polynomial determination method, an influence of the beam hardening effect is taken into consideration by using the water phantoms, but a shape and a material of the water phantom are not limited thereto as long as the polynomial can be approximated on the basis of a relationship between an average value and a variance of measurement data.

As mentioned above, in Embodiment 3, the data fidelity term is determined on the basis of a relationship between an average value and a variance of actually measured data, and thus it is possible to realize a desired noise reduction effect more accurately by taking into consideration an influence of the beam hardening effect of X-rays detected by the X-ray detector 14.

Other configurations and processing operations are the same as in Embodiment 1, and thus description thereof will be omitted.

Embodiment 4

In Embodiment 4, the correction processing device 42 performs a process for achieving a desired noise reduction effect more accurately even in a case where an average of measurement data of detection elements j around a focused detection element i is considerably small in Embodiment 3.

A configuration of the correction processing device 42 of Embodiment 4 and a flow of a process performed by the correction processing device 42 are the same as in Embodiment 3, but Equation (13) is used instead of Equation (12). Equation (13) relates to f(T$_i$) multiplied in a data fidelity term of Embodiment 4.

[Equation 13]

$$f(T_i) = \sum_{b=1}^{B} \theta_b T_i^b + \zeta \sum_{b=1}^{B} \theta_b T_i^b \Big/ \sum_{b=0}^{B} \theta_b T_0^b \qquad (13)$$

In Equation (13), symbols common to Equation (12) indicate the same parameters as in Embodiment 3. The first term of Equation (13) is the same as that of Equation (12), and the second term thereof is obtained by multiplying a variance ratio gain ζ by a ratio between a variance in which system noise is not included in a polynomial and a variance in which the system noise is included therein. In the first term, system noise included in data is not taken into consideration, and thus a desired noise reduction effect may not be achieved in a case where an average of measurement data of the detection elements j around the focused detection element i is considerably small. Therefore, Equation (12) is corrected by taking into consideration an influence of the system noise in the second term.

The variance ratio gain ζ of Equation (13) is determined by the noise reduction processor 132 in the same manner as β described above. Here, a description will be made of an operation in which the noise reduction processor 132 determines the variance ratio gain ζ along a flow illustrated in FIG. 9.

First, in the same manner as in the case of determining coefficients and orders of a polynomial in Embodiment 3, output signals from the data acquisition system 25 are acquired by performing scanning on each of phantoms having different diameters. The process in step 401 of FIG. 4 is performed on each of the obtained output signals, and thus measurement data is obtained. Through such a procedure, noise measurement data corresponding to the type of diameter of the phantom having undergone the scanning is acquired (step 901). In order to differentiate noise measurement data for different phantom diameters from each other, hereinafter, the noise measurement data will be referred to as noise measurement data A, B, . . . .

Next, a value of the function R(s) of Equation (11) is calculated by using the noise measurement data A, B, . . . obtained in step 901, the predefined provisional variance ratio gain ζ, and the above-described other parameters, and transformed data which causes the function R(s) to be the minimum is obtained through successive processes (step 902). The process in step 902 is performed on each of the noise measurement data A, B, . . . . In addition, the provisional variance ratio gain ζ is set to a sufficiently small positive number.

Figure 6:
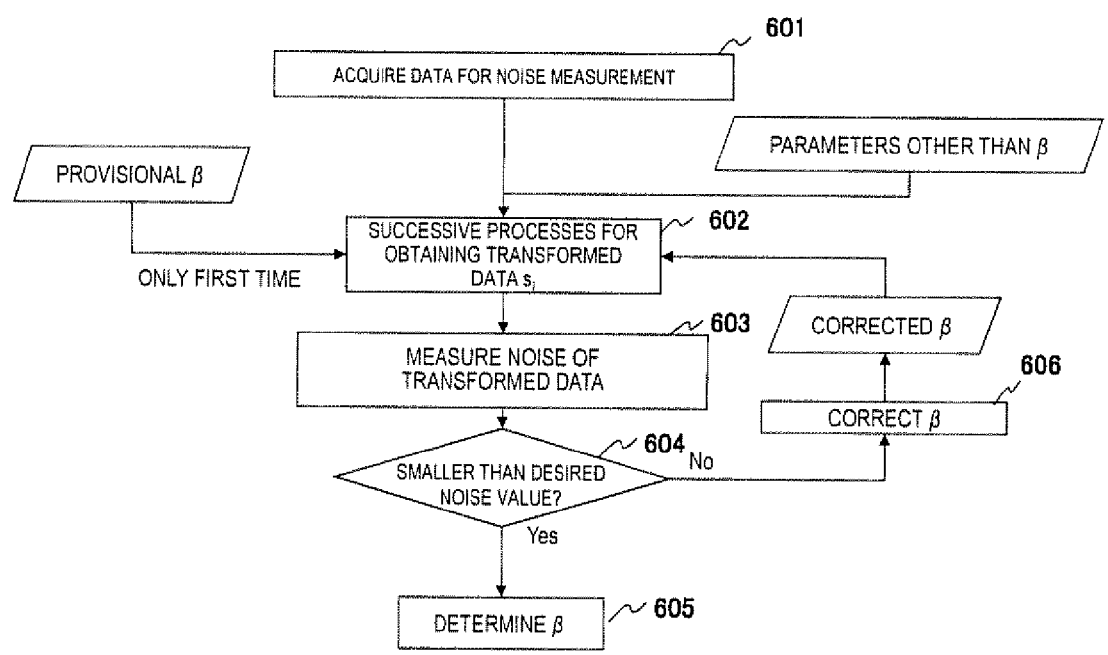
FIG. 6 is a flowchart illustrating an operation of obtaining a penalty coefficient β of Embodiment 1.

An operation of obtaining the transformed data through successive processes in step 902 is the same as the operation described in step 602 of FIG. 6, and thus description thereof will be omitted. In step 902, each transformed data item corresponding to the provisional variance ratio gain ζ is obtained with respect to the noise measurement data A, B, . . . .

Figure 9:
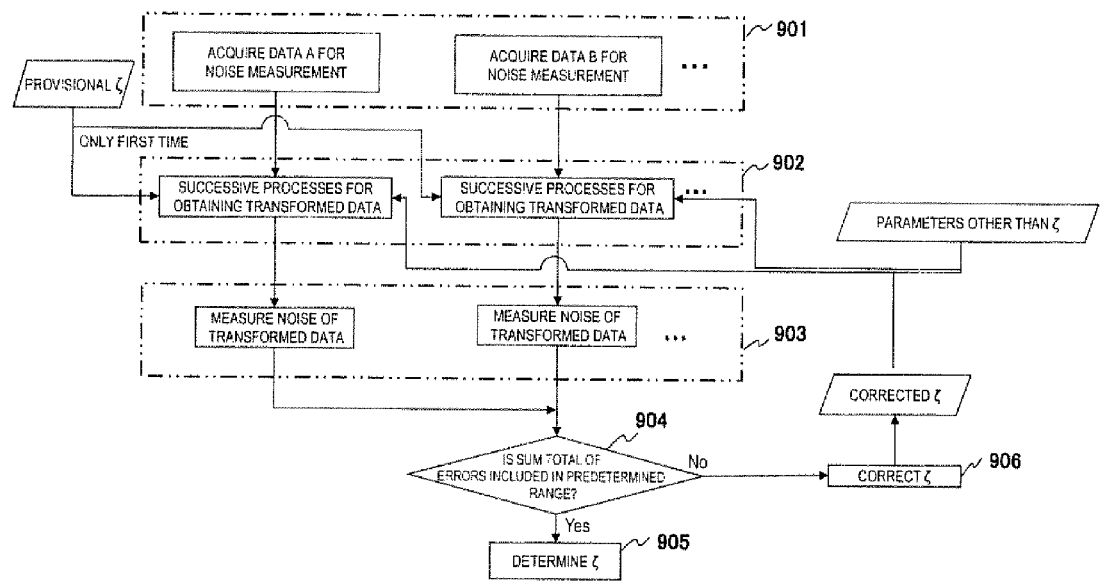
FIG. 9 is a flowchart illustrating an operation of obtaining a variance ratio gain ζ of Embodiment 4.

Next, the flow proceeds to step 903 of FIG. 9, and noise measurement is performed on the transformed data. Also in this step, transformed data corresponding to the noise measurement data A, B, . . . are separately processed. For convenience of description, herein, the noise measurement data A is focused. An average value and a variance are obtained on the basis of the transformed data of the noise measurement data A. In addition, an error between the obtained variance and a reference value is calculated.

As the reference value, a value obtained by assigning the calculated mean value to Equation (12) is used. In addition, as the error, for example, an absolute error of the variance relative to the reference value is used. Respective errors of the transformed data corresponding to the noise measurement data A, B, . . . are calculated by applying the process to the noise measurement data A, B, . . . .

The reference value in step 903 corresponds to a variance which does not include system noise calculated on the basis of an average value of data. Therefore, in a case where the calculated variance has a value close to the reference value for the phantoms with all the diameters, that is, an error is small in step 903, the data is determined to undergo a desired noise reduction process.

A sum total of errors corresponding to the noise measurement data A, B, . . . calculated in step 903 is obtained, and it is determined whether or not a predefined sum total of errors is included in a predetermined range (step 904). The predetermined error range in step 904 may employ a value which is empirically set, and is set to, for example, 0.1.

In a case where the obtained sum total of errors is smaller than the predetermined range, the provisional variance ratio gain ζ is determined as being optimal ζ, and the process is finished (step 905).

On the other hand, in a case where the obtained sum total of errors is greater than the predetermined range, any positive value is added to the provisional variance ratio gain ζ in order to correct ζ (step 906). Corrected is used as the provisional variance ratio gain ζ, and the flow returns to step 902 so that the processes in steps 902 to 904 are repeatedly performed.

The above-described processes in steps 902 to 904 correspond to a method in which the variance ratio gain ζ is gradually increased from a positive number close to 0, and ζ obtained at the time when a sum total of errors smaller than the predetermined range is obtained for the first time is determined as an optimal variance ratio gain ζ, but the present invention is not limited thereto, and a method may be used in which ζ is gradually decreased.

In addition, only step 402 of FIG. 4 is executed in the above-described step 902, but step 403 of FIG. 4 may also be executed, and obtained non-positive number transformed data may be used instead of transformed data. In this case, the variance ratio gain ζ is determined by the noise reduction processor 132 and the positive number converter 133.

In addition, since the system noise changes depending on a rotation speed or a tube voltage, the noise reduction processor 132 obtains an optimal variance ratio gain ζ for each scanning condition in advance, and stores the optimal variance ratio gain in the evaluation function parameter setter 136.

Other configurations and processing operations are the same as in Embodiment 3, and thus description thereof will be omitted.

In the above-described embodiments, the present invention has been described and illustrated in detail, but the embodiments are intended for description and illustration only, and the present invention is not limited to the content of the embodiments.

REFERENCE SIGNS LIST

1 SCANNER, 2 BED, 3 INPUT DEVICE, 4 CALCULATION DEVICE, 5 DISPLAY DEVICE, 11 X-RAY GENERATION DEVICE, 14 X-RAY DETECTOR, 23 COLLIMATOR, 41 AEC CALCULATION DEVICE, 42 CORRECTION PROCESSING DEVICE, 43 RECONSTRUCTION CALCULATING DEVICE, 44 IMAGE PROCESSING DEVICE, 131 PREPROCESSOR, 132 NOISE REDUCTION PROCESSOR, 133 POSITIVE NUMBER CONVERTER, 134 CORRECTION PROCESSOR, 135 THRESHOLD VALUE SETTER, 136 EVALUATION FUNCTION PARAMETER SETTER

The invention claimed is:

1. An X-ray CT apparatus comprising:
an X-ray generation unit that irradiates X-rays to an object;
an X-ray detector that detects the X-rays through the object;
a correction processing unit that corrects an output signal value from the X-ray detector; and
a reconstruction calculating unit that reconstructs an image on the basis of an output from the correction processing unit,
wherein the X-ray detector includes arranged detection elements, and
wherein the correction processing unit maintains an average value of output signal values of a plurality of predetermined detection elements centering on a focused detection element among the detection elements, and also reduces a variance of the output signal values of the plurality of predetermined detection elements centering on the focused detection element.

2. The X-ray CT apparatus according to claim 1, wherein the correction processing unit obtains a value of each of a first evaluation function and a second evaluation function which have a corrected output signal value of the focused detection element as a variable, and obtains the corrected output signal value which causes a sum of the values to be the minimum through successive processes while changing the corrected output signal value,
wherein the first evaluation function is a function in which a value of the first evaluation function becomes smaller as a difference between an uncorrected output signal value and a corrected output signal value of the focused detection element becomes smaller, and
wherein the second evaluation function is a function in which a value of the second evaluation function becomes smaller as a difference between corrected output signal values of the focused detection element and a detection element adjacent thereto becomes smaller.

3. The X-ray CT apparatus according to claim 2, wherein the first evaluation function is obtained by multiplying the square of the difference between the uncorrected output signal value and the corrected output signal value of the focused detection element by a predetermined coefficient T.

4. The X-ray CT apparatus according to claim 3, wherein the coefficient T is a value obtained by weighted-adding output signal values of a set of the focused detection element i and one or more detection elements j centering on the focused detection element.

5. The X-ray CT apparatus according to claim 4, wherein the coefficient T is an average value of output signal values of the set of the detection element i and the detection elements j.

6. The X-ray CT apparatus according to claim 4, wherein the coefficient T is a value obtained by weighted-adding an output signal value of each of the one or more detection elements j according to a spatial distance between the detection element i and the detection element j.

7. The X-ray CT apparatus according to claim 4, wherein the coefficient T is a value obtained by weighted-adding an output signal value of each of the one or more detection elements j on the basis of a correlation between an output signal value of the detection element i and an output signal value of the detection element j.

8. The X-ray CT apparatus according to claim 3, wherein the coefficient T is a value obtained by transforming a value obtained by weighted-adding output signal values of a set of the focused detection element i and one or more detection elements j centering on the focused detection element i, by using a transform function including a polynomial in which a relationship between an average and a variance of signal values experimentally obtained is approximated.

9. The X-ray CT apparatus according to claim 8, wherein the transform function includes a differential polynomial obtained by subtracting a variance corresponding to system noise experimentally obtained from the polynomial.

10. The X-ray CT apparatus according to claim 2, wherein, when obtaining the sum of the values of the first evaluation function and the second evaluation function, the correction processing unit performs weighted-adding by using a weighting factor $\beta$.

11. The X-ray CT apparatus according to claim 10, wherein the weighting factor $\beta$ is a value in which a variance of the corrected output signal values obtained by the correction processing unit is equal to or less than a predefined value with respect to a plurality of output signal values of the detection elements obtained in a state in which X-rays irradiated to the object by the X-ray generation unit are shielded.

12. The X-ray CT apparatus according to claim 2, wherein, when obtaining the sum of the values of the first evaluation function and the second evaluation function, the correction processing unit performs weighted-adding by using a weighting factor $\alpha$, the weighting factor $\alpha$ being defined for each of the detection elements.

13. The X-ray CT apparatus according to claim 12, wherein the weighting factor $\alpha$ becomes greater as an output signal value of the detection element is a non-positive number and an absolute value thereof becomes greater.

14. The X-ray CT apparatus according to claim 1, wherein the detection elements of the X-ray detector are arranged in two-dimensional directions including a channel direction and a row direction,
wherein the X-ray generation unit and the X-ray detector detect X-rays transmitted through the object at a plurality of positions (views) while being rotated around the object, and
wherein at least one of the plurality of predetermined detection elements is adjacent to the focused detection element in any one of a channel, row, and view directions.

15. The X-ray CT apparatus according to claim 1, further comprising:
an automatic exposure control calculation device that modulates a tube current for the X-ray generation unit during scanning according to information regarding the object.

16. A correction processing device which corrects output signals of detection elements arranged in two-dimensional directions of an X-ray CT apparatus,
wherein the correction processing device maintains an average value of output signal values of a plurality of predetermined detection elements centering on a focused detection element among the detection elements, and also reduces a variance of the output signal values of the plurality of predetermined detection elements centering on the focused detection element.

\* \* \* \* \*